(12) United States Patent
Kloza et al.

(10) Patent No.: US 7,397,247 B2
(45) Date of Patent: Jul. 8, 2008

(54) APPARATUS AND PROBE HEAD FOR DETERMINING A QUANTITATIVE PROPERTY OF A SAMPLE SUBSTANCE BY MEANS OF MAGNETIC RESONANCE

(75) Inventors: Marian Kloza, Waldbronn (DE); Dieter Schmalbein, Marxzell-Burbach (DE); Diether Maier, Rheinstetten (DE)

(73) Assignee: Bruker BioSpin GmbH, Rheinstetten-Forchheim (DE)

( * ) Notice: Subject to any disclaimer, the term of this patent is extended or adjusted under 35 U.S.C. 154(b) by 0 days.

(21) Appl. No.: 11/346,613

(22) Filed: Feb. 2, 2006

(65) Prior Publication Data

US 2006/0192557 A1    Aug. 31, 2006

(30) Foreign Application Priority Data

Feb. 3, 2005    (DE)    ......................... 10 2005 006 725

(51) Int. Cl.
*G01V 3/00*    (2006.01)
(52) U.S. Cl. ........................................ 324/321; 324/318
(58) Field of Classification Search ......... 324/318–322, 324/309, 307; 600/410, 422; 333/219.2, 333/224, 227, 232
See application file for complete search history.

(56) References Cited

U.S. PATENT DOCUMENTS

| | | | | |
|---|---|---|---|---|
| 4,435,680 | A * | 3/1984 | Froncisz et al. | 324/316 |
| 4,446,429 | A * | 5/1984 | Froncisz et al. | 324/316 |
| 6,759,601 | B1 | 7/2004 | Petty et al. | |
| 6,946,838 | B2 * | 9/2005 | Corver et al. | 324/307 |
| 7,002,346 | B2 * | 2/2006 | Schaepman et al. | 324/315 |
| 7,008,486 | B2 * | 3/2006 | Corver | 134/1 |
| 7,015,693 | B2 * | 3/2006 | Corver et al. | 324/300 |
| 7,064,548 | B2 * | 6/2006 | Aptaker et al. | 324/318 |
| 7,199,581 | B2 * | 4/2007 | Corver et al. | 324/308 |
| 2004/0231699 | A1 * | 11/2004 | Corver | 134/3 |
| 2004/0251904 | A1 | 12/2004 | Corver et al. | |

(Continued)

FOREIGN PATENT DOCUMENTS

WO    WO 99/67606 A1    12/1999

(Continued)

*Primary Examiner*—Brij Shrivastav
*Assistant Examiner*—Tiffany A Fetzner
(74) *Attorney, Agent, or Firm*—Law Offices of Paul E. Kudirka

(57) ABSTRACT

An apparatus for determining a quantitative property of a sample substance by means of magnetic resonance is disclosed. The apparatus comprises a conveyor for conveying sample containers containing the sample substance through a measuring station. The measuring station comprises a magnet system for generating a constant magnetic field of high homogeneity. The measuring station, further, comprises a probe head adapted for letting sample containers be conveyed therethrough and for generating a high frequency magnetic field. A magnetic resonance measuring unit determines the quantitative property of the sample substance contained in the probe head. The probe head excites and detects, resp., the magnetic resonance essentially only within that section of the sample container which contains the sample substance. The probe head comprises a split-ring resonator which, as seen in a conveying direction of the conveyor, has a passage cross-section for letting run the sample containers therethrough. The high frequency magnetic field is generated essentially only in an area of the passage cross-section through which the sample containers run during conveying.

11 Claims, 4 Drawing Sheets

U.S. PATENT DOCUMENTS

2005/0116712 A1* 6/2005 Corver et al. ............... 324/309
2005/0122104 A1   6/2005 Corver et al.
2005/0242808 A1* 11/2005 McKendry et al. .......... 324/307
2005/0242809 A1* 11/2005 McKendry et al. .......... 324/308
2005/0242811 A1* 11/2005 Schaepman et al. ......... 324/315
2005/0242813 A1* 11/2005 Aptaker et al. .............. 324/318
2006/0192557 A1*  8/2006 Kloza et al. ................. 324/318

FOREIGN PATENT DOCUMENTS

WO    WO 2004/104989 A2    12/2004

* cited by examiner

APPARATUS AND PROBE HEAD FOR DETERMINING A QUANTITATIVE PROPERTY OF A SAMPLE SUBSTANCE BY MEANS OF MAGNETIC RESONANCE

FIELD OF THE INVENTION

The invention relates to the field of magnetic resonance like nuclear magnetic resonance (NMR) or electron spin resonance (ESR).

More specifically, the invention relates to the field of determining a quantitative property, for example a mass, of a sample by means of magnetic resonance.

Still more specifically, the invention relates to an apparatus for determining a quantitative property of a sample substance by means of magnetic resonance, comprising a conveyor for conveying sample containers containing the sample substance through a measuring station, wherein the measuring station comprises a magnet system for generating a constant magnetic field of high homogeneity, a probe head adapted for letting sample containers be conveyed therethrough and for generating a high frequency magnetic field, and a magnetic resonance measuring unit for determining the quantitative property of the sample substance contained in the probe head, wherein the probe head excites and detects, resp., the magnetic resonance essentially only within that section of the sample container which contains the sample substance.

Moreover, the invention relates to a probe head, for determining a quantitative property of a sample substance within a predetermined section of a sample container by means of magnetic resonance, the probe head being adapted for having the sample containers conveyed therethrough and for generating and receiving, resp., a high frequency magnetic field essentially only in the predetermined section of the sample container.

BACKGROUND OF THE INVENTION

Within various chemical and pharmaceutical processes it is necessary to exactly determine a quantitative property of a certain amount of substance, for example the weight or the mass thereof. This is, for example, of particular importance in the course of the automatic filling of pharmaceutical agents into appropriate containers because it is mandatory that the amount of substance filled be exact.

Certain pharmaceutical agents that are intended to be used for a medical injection are, for example, filled into vials as powders. When doing so, the amount of powder fills only a portion of the vial. The vials are closed by means of a lid being made of metal or of a hard plastic material. The lid has a central opening being closed by an elastic seal. Immediately prior to using the agent, the medical doctor draws an appropriate solvent into a syringe, pierces the seal by means of the syringe needle and injects the solvent into the free volume of the vial. By vigorously agitating the vial, the agent powder is dissolved in the solvent. The solution which is thus prepared, is then again drawn into the syringe and may be injected into a patient. It goes without saying that during the filling process within the premises of a pharmaceutical production plant, the amount of the agent contained within the vial must be metered exactly.

Within a filling installation, pharmaceuticals are produced in large quantities, typically with filling rates of several hundred units per minute.

A thorough weight control may not be effected under these circumstances by conventional balances. One has, therefore, only been able in the past to take random samples and to check same by proper weighing, for example by weighing each hundredth packing unit. However, this procedure more and more has been considered insufficient. Therefore, the pharmaceutical industry works on appropriate standards (so-called "PAT-Initiative"), which set standards for certain pharmaceuticals, for example the above-explained injection pharmaceuticals, by making mandatory a weight control of each individual packing unit.

U.S. Pat No. 6,759,601 discloses a check weighing apparatus and method in which the weight of a filled amount of a substance may be determined in a contactless manner. Such apparatuses are identified in the art as "NCCW" (non contact check weigher). In such installations, the samples are conveyed on a conveyor belt into the area of a measuring station.

The measuring station contains a nuclear magnetic resonance (NMR) measuring installation. The installation consists of at least one high frequency coil and an iron magnet system having its magnetic poles arranged on both sides of the conveyor belt. The samples run on the moving conveyor belt through the high frequency magnetic field generated by the high frequency coil. The magnet system generates a constant magnetic field of high homogeneity at the position where the samples run therethrough, the constant magnetic field having a direction being transverse with regard to the conveying direction of the conveyor belt. The high frequency magnetic field generated by the high frequency coil extends perpendicular thereto.

By properly tuning the field strength of the constant magnetic field to the frequency of the high frequency magnetic field, nuclear magnetic resonance (NMR) is excited within the sample substance. The resonance signals are received by the high frequency coil and are fed to an appropriate evaluation unit. The nuclear magnetic resonance signal is a measure for the quantity of sample substance. By comparing with a nuclear resonance signal of a calibration sample of known weight and consisting of the same substance, the weight of the sample substance to be measured may be determined.

However, during the measuring of the magnetic resonance, the solid state material used for making the lid or the seal of the sample container, may give rise to spurious signals. If, for example, rubber or plastic materials are used, then the hydrogen atoms thereof give rise to NMR signals which may render inaccurate the measuring result as such.

In some embodiments of the apparatus disclosed in U.S. Pat. No. 6,759,601, cf. FIGS. 1, 7 and 8, the probe head configured as a high frequency solenoid coil surrounds the entirety of sample substance and sample container. These embodiments, therefore, are only adapted to be used for the measurement of liquid sample substances because it is the entirety of sample substance and sample container that is exposed to the high frequency magnetic field. Spurious signals emanating from the sample container, in particular from the lid, will not become apparent in this situation if the high frequency pulses used for the measurement are only adapted to the long relaxation times of liquids. The relaxation times of solids, in contrast, are essentially shorter, so that these solids do not contribute any spurious signals when such high frequency pulses are used. However, such long relaxation times require that the samples that are fed to the apparatus at high velocity, be magnetically biased prior to reaching the high frequency coil. For that purpose the prior art apparatus has a magnet system being configured so large that the constant magnetic field is already effective in an area upstream of the high frequency coil.

On the other hand, there is a substantial need for installations, for example NCCW installations, which are likewise capable of measuring quantitative properties of solid sample substances, for example for measuring the weight of the injection pharmaceuticals discussed at the outset.

Further embodiments of the apparatus disclosed in U.S. Pat. No. 6,759,601, cf. FIG. 9, therefore, are adapted to excite magnetic resonance only within a portion of the sample container in which the sample substance is contained. By doing so, the excitation of spurious signals from the lid or from the seal shall be avoided. For that purpose, according to a first alternative, gradient coils are arranged within the measuring station, in order to superimpose magnetic field gradients on the constant magnetic field, thus permitting a local excitation of magnetic resonance. According to a second alternative, high frequency solenoid coils are arranged within the measuring station below the conveyor belt, so that they are arranged closer to the sample substance as compared to the lid or to the seal, resp.

The afore-mentioned first alternative has the disadvantage that the structural complexity of the installation is greatly increased by the need of providing an additional gradient system together with an appropriate supply and signal evaluation. The operation of the installation becomes likewise more complicated.

The second alternative, first, has the principal disadvantage that the excitation of spurious signals from the lid or from the seal, resp., may be reduced only slightly because the sample substance is located in the direct vicinity of the lid and of the sealing, resp., in particular when the probe container is fully filled with sample substance. In such a situation, the high frequency magnetic field being generated by a solenoid coil arranged below the conveyor belt and being directed upwardly, reaches the lid or the seal, resp., at almost unreduced amplitude. Another disadvantage consists in the fact that a high frequency magnetic field being irradiated from below at a distance is significantly less homogeneous as compared to a field that is generated, for example, by a solenoid coil surrounding the sample. This may lead to errors in the measuring result. Finally, the magnetic field must be irradiated at a high intensity. All these problems become more important, the bigger the distance is between the high frequency coil and the sample substance. Moreover, this second alternative requires separate structural units, one above and one below the conveyor belt.

SUMMARY OF THE INVENTION

It is, therefore, an object underlying the invention to improve an apparatus and a probe head of the type specified at the outset, such that these disadvantages are avoided. In particular it shall become possible in filling installations running at high filling rates to determine certain quantitative properties of solid sample substances in a reliable manner, with high accuracy and with simple means.

According to the apparatus specified at the outset, this object is achieved by an apparatus for determining a quantitative property of a sample substance by means of magnetic resonance, comprising:

a plurality of sample containers having a predetermined section containing the sample substance;

a measuring station;

a conveyor for conveying the sample containers through the measuring station;

a magnet system within the measuring station for generating a constant magnetic field of high homogeneity;

a probe head within the measuring station adapted for having the sample container conveyed therethrough and for generating and receiving, resp., a high frequency magnetic field essentially only in the section of said sample container;

a split-ring resonator arranged within the probe head, the split-ring resonator, as seen in a conveying direction of the conveyor, having a passage cross-section for allowing the sample containers to run therethrough, the high frequency magnetic field being generated and received, resp., essentially only in a predetermined portion of the passage cross-section; and a magnetic resonance measuring unit for determining the quantitative property of the sample substance contained in the probe head.

In a probe head specified at the outset, the object is achieved in that a split-ring resonator is arranged within the probe head, the split-ring resonator having a passage cross-section for allowing the sample containers to run therethrough, the high frequency magnetic field being generated and received, resp., essentially only in a predetermined portion of the passage cross-section.

The object underlying the invention is thus entirely solved.

The invention has the advantage that the high frequency magnetic field being required for exciting the magnetic resonance is generated directly within that portion of the probe head through which the probe container runs, wherein said portion of the probe head configures a section of a split-ring resonator. By doing so, a narrowly limited local excitation only of the sample substance within a homogeneous field of relatively low amplitude becomes possible.

The apparatus according to the present invention may be used within a pharmaceutical production facility having strict requirements with respect to cleanliness, and in which, therefore, the production installations are cleaned with liquid agents on a regular basis, in particular are sterilized. In such a situation, the probe head of the present invention may be disassembled as a whole and may be cleaned or sterilized, resp. Separate operations below the conveyor belt are, therefore, not necessary.

The invention, further, has the advantage that not only individual samples but a plurality of samples may be measured which are fed by means of a conveyor.

According to a preferred embodiment of the invention, the split ring resonator comprises a ring fed by a high frequency signal, the ring defining a central axis and having first gaps on two diametrically opposite peripheral positions thereof, the first gaps extending parallel to the axis. Annexes of the ring are provided having a broad surface and being annexed to the ring from outside at the peripheral positions of the first gaps. The surfaces have each a central second gap extending parallel to the axis, wherein the second gaps at one end thereof communicate with the first gaps.

This measure has the advantage that the required configuration of the probe head may be simply effected under high frequency aspects.

Preferably, the annexes are configured wing-shaped, in particular extend parallel to the axis.

All these measures have the advantage that a very homogeneous high frequency field may be generated.

Moreover, embodiments of the apparatus according to the present invention are preferred in which at least the measuring station is adapted to be cleaned by means of a liquid cleaning agent.

The advantages explained before in connection with the inventive apparatus likewise apply, mutatis mutandis, for the probe head according to the present invention.

The measured quantitative property, preferably, is the weight or the mass, respectively, of the sample substance or of a predetermined part thereof.

It is particularly preferred when the sample substance is a solid state substance, although the invention would also allow to measure liquid substances.

Moreover, it is preferred when, in a manner known as such, the quantitative property of the sample substance is determined by comparing the resonance signal emitted by the sample substance with a resonance signal of a reference sample of the sample substance having known quantitative properties.

The invention is based on magnetic resonance. Preferably, the magnetic resonance is excited as nuclear magnetic resonance (NMR). However, also electron spin resonance (ESR) could be excited.

Further advantages become apparent from the description and the enclosed drawing.

It goes without saying that the features mentioned before and those that will be explained hereinafter, may not only be used in the particularly given combination, but also in other combinations or alone, without leaving the scope of the present invention.

BRIEF DESCRIPTION OF THE DRAWINGS

The above and further advantages of the invention may be better understood by referring to the following description in conjunction with the accompanying drawings in which.

Embodiments of the invention are shown in the drawing and will be discussed in further detail in the subsequent description.

DETAILED DESCRIPTION

Figure 1:
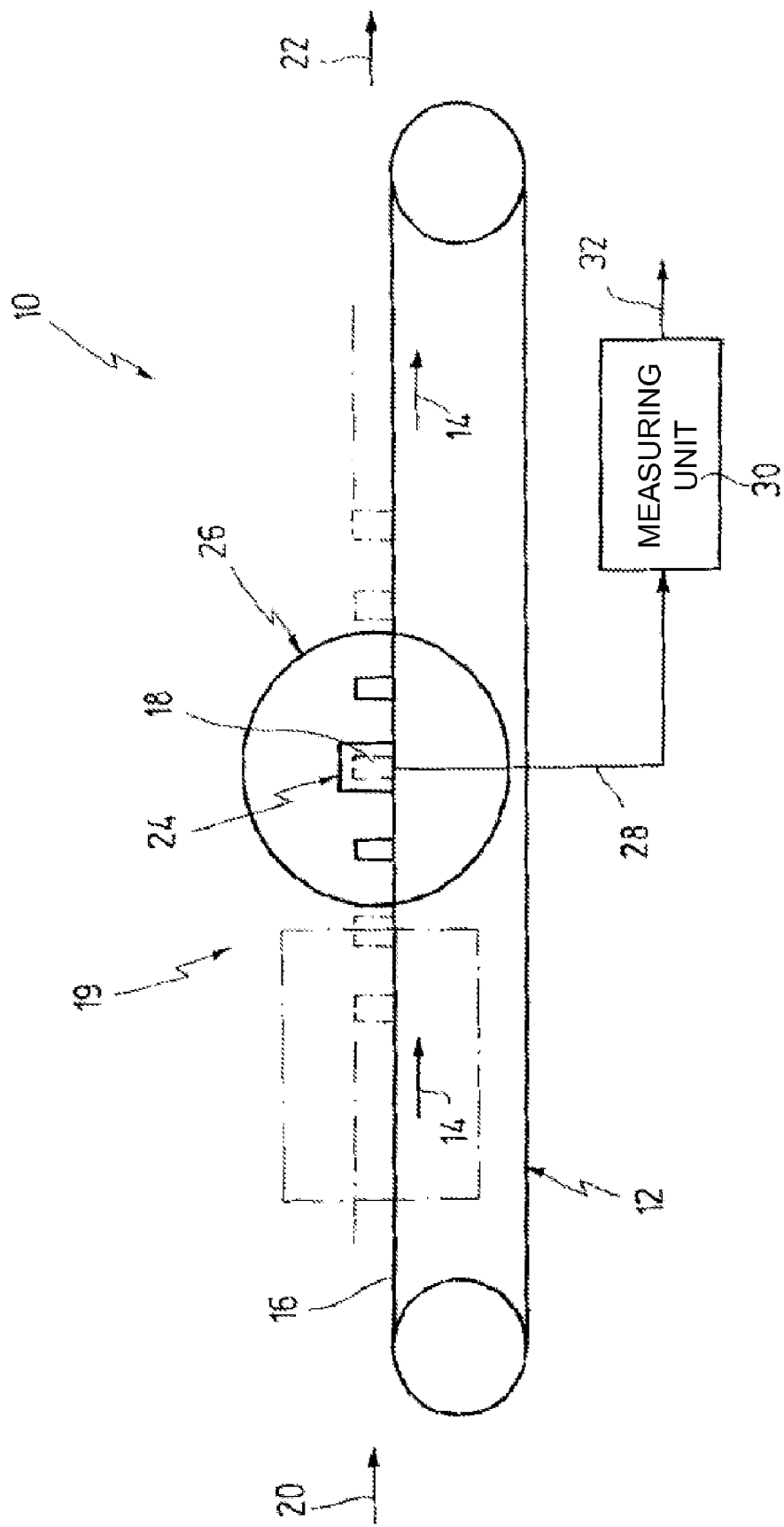
FIG. 1 shows a highly schematic side-elevational view of an embodiment of an inventive apparatus.

In FIG. 1, reference numeral 10 as a whole indicates an apparatus for determining a quantitative property of a sample substance contained in a sample container by means of magnetic resonance, as is, for example, used by a pharmaceutical production or filling facility. The quantitative property, preferably, is the weight or the mass, resp., of the sample substance or of a predetermined portion thereof. In the following, the invention is explained with an example of a weight determination, without, however, thereby narrowing the scope of the invention.

Apparatus 10 comprises a belt conveyor 12 or another suitable conveyor. Sample containers 18 are conveyed on belt conveyor 12 on an upper conveyor belt section 16 in the direction of arrows 14 from the left to the right in FIG. 1. Upper conveyor belt section 16 of the conveyor belt runs through a measuring station 19. Sample containers 18 are set onto belt conveyor 12 on the left hand side in a loading position 20 and are taken therefrom on the right hand side in an unloading position 22.

Within measuring station 19, sample containers 18 run through a probe head 24. On both sides of upper conveyor belt section 16, a magnet system 26 is arranged at the same vertical position as probe head 24. A transmitter/receiver line 28 interconnects probe head 24 and measuring unit 30 which is adapted to conduct measurements by means of magnetic resonance. Magnet system 26 generates a constant magnetic field $B_0$ being oriented transversely to the direction of belt conveyor 12. Probe head 24, in contrast, generates and receives a high frequency magnetic field $B_1$ being oriented perpendicular to constant magnetic field $B_0$ (the high frequency magnetic field $B_1$ is illustrated as field lines 54 in FIG. 3).

In the embodiment shown, nuclear magnetic resonance (NMR) is used operated at a measuring frequency of, for example, 18 to 20 MHz, corresponding to a field strength of about 0.45 T of constant magnetic field $B_0$ for protons. Measurements with electron spin resonance (ESR) are likewise possible.

A data line 32 at the output of measuring unit 30 supplies the measured data about the weight of each individual sample container 18. These data are correspondingly processed. Sample containers having a weight which is not within predetermined limits, are excluded from further processing (not shown). Moreover, the data are permanently stored within a quality management system.

Preferably, measuring station 19 is operated with pulsed nuclear magnetic resonance, as was already described at the outset in connection with the prior art. However, apparatus 10 preferably processes sample containers having solid samples therein. For that purpose, probe head 24 is especially configured, as will be explained hereinafter in connection with FIGS. 2 to 5.

Figure 2:
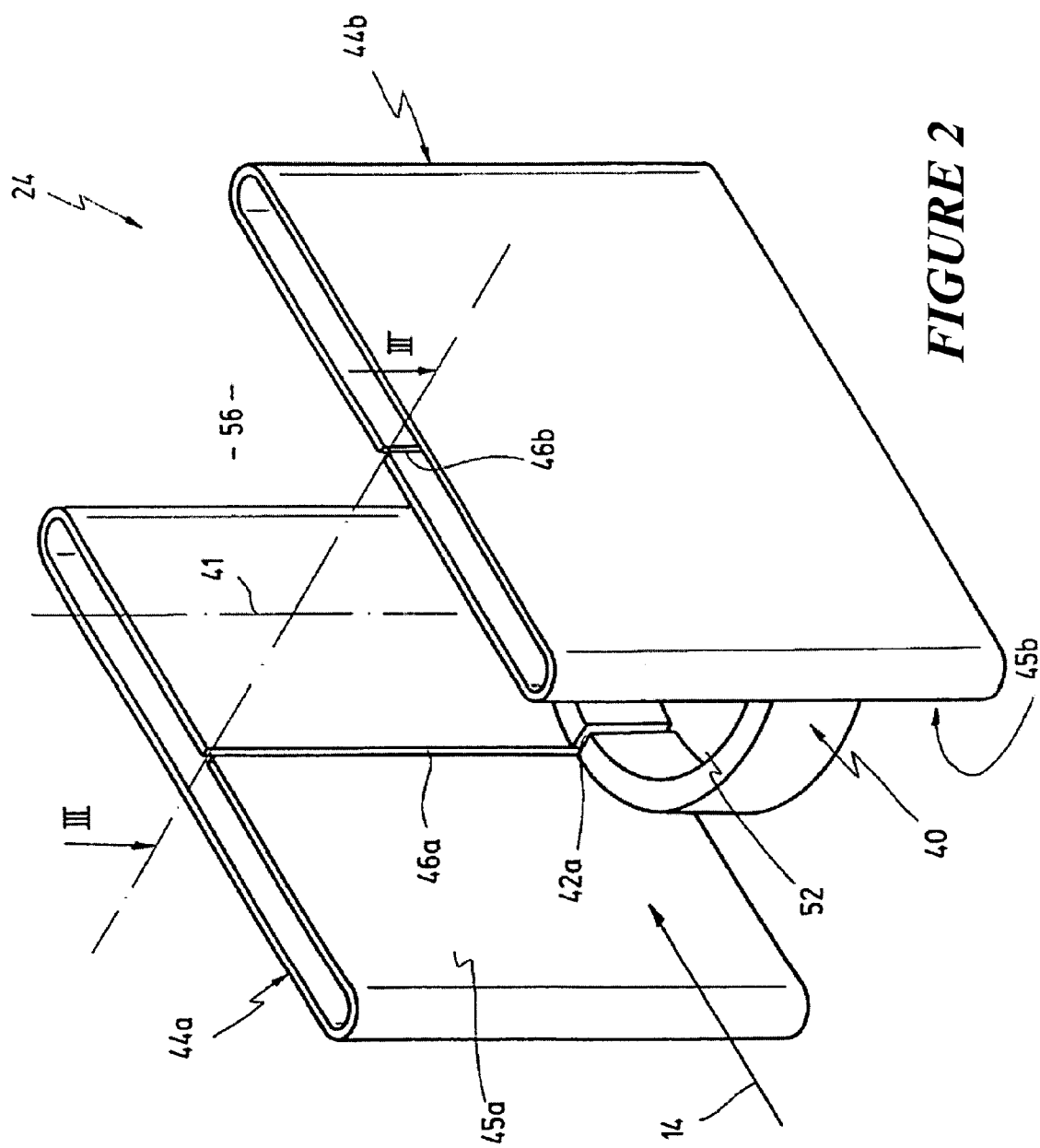
FIG. 2 shows a schematic perspective view of an embodiment of an inventive probe head, as can be used in the apparatus of FIG. 1.
Figure 3:
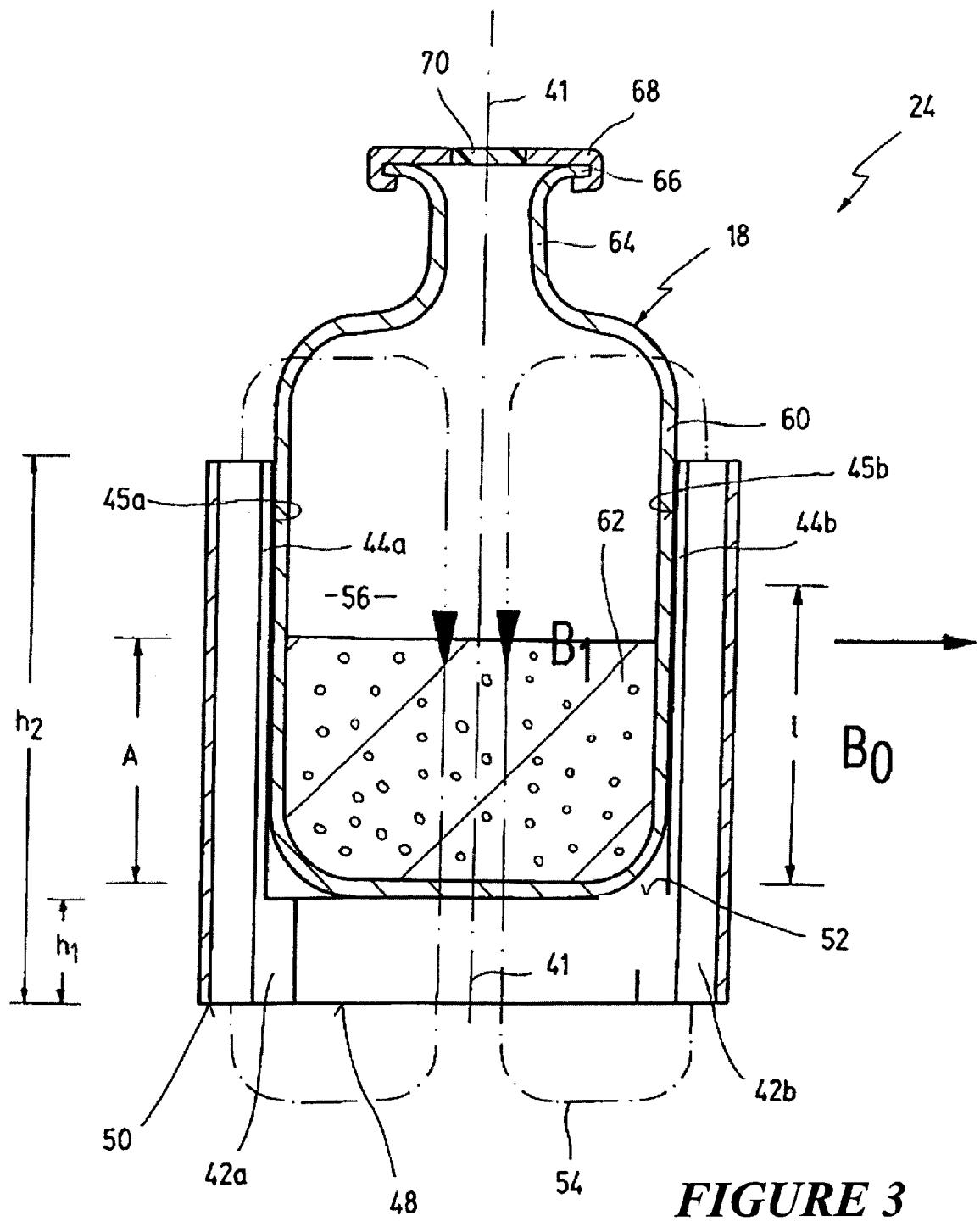
FIG. 3 is a cross-sectional view of the probe head of FIG. 2 along the plane indicated by a line III-III in FIGS. 1 and 4.
Figure 4:
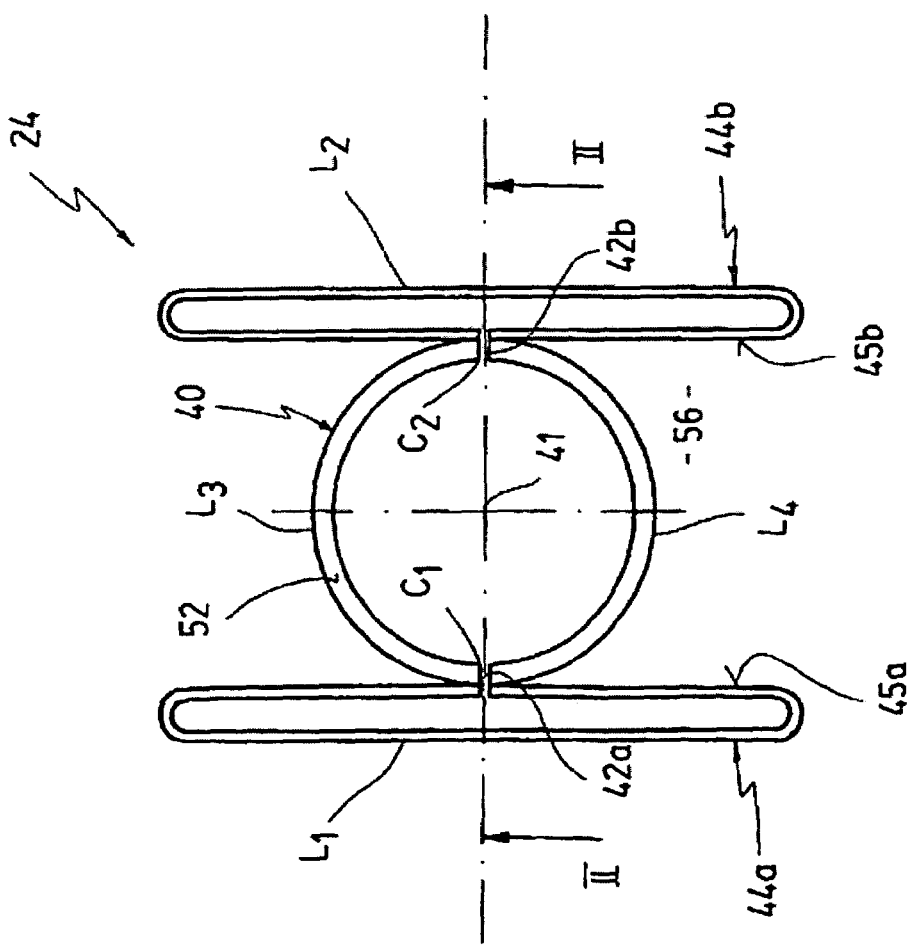
FIG. 4 is a top plan view of the probe head of FIG. 2.

In probe head 24, as shown in FIGS. 2 to 4, one can see a ring 40 defining a central axis 41. Ring 40 is provided with two gaps 42a and 42b being positioned at diametrically opposite positions and each extending parallel to axis 41. This configuration is referred to in the art as "split-ring resonator" or as "loop-gap resonator".

At the positions of gaps 42a and 42b, there are wing-shaped annexes 44a and 44b annexed to ring 40. Annexes 44a and 44b have a flat oval cross-section. They are provided with broad surfaces 45a and 45b facing ring 40. Surfaces 45a and 45b are likewise provided with gaps 46a and 46b, also extending parallel to axis 41.

In the direction of axis 41, ring 40 has a height $h_1$, whereas annexes 44a and 44b have a significantly bigger height $h_2$. The configuration is such that a bottom side 48 of ring 40 is flush with bottom sides 50 of annexes 44a and 44b. The entire arrangement is, therefore, non-symmetrical in an axial direction. Gaps 42a and 46a as well as gaps 42b and 46b communicate with each other, i.e. they are openly disposed one onto the other.

As one may clearly see from FIGS. 2 and 3, probe head 24, as seen in conveying direction 14, has the shape of a U being open upwardly. Sample containers 18 may now be conveyed on a top side 52 of ring 40 through a passage cross-section 56 which corresponds to the free space between the two annexes 44a, 44b protruding upwardly above ring 40. Passage cross-section 56 is laterally limited by surfaces 45a and 45b.

For the sake of simplicity, FIGS. 2 and 3 do not show upper conveyor belt section 16 which, for example, could run through a corresponding recess within top side 52. Likewise, the elements required for coupling-in the high frequency transmitter signals and for coupling-out the high frequency receiver signals, are not shown. These elements are well known to the person of ordinary skill.

In FIG. 3 it is shown that sample container 18 is provided with a bulged portion 60 in its bottom part, portion 60 being only partially filled with a powder sample substance 62. The filled section of bulged portion 16 is designated "A" in FIG. 3.

At its upper end, bulged portion 60 has a transition to a neck 64 which, in turn, has a transition to a radially enlarged flange 66. At flange 66, sample container 18 is closed by means of a cap 68 being laterally bent about flange 66. Cap 68 consists of a hard plastic material or of a non-magnetic metal. In the center of cap 68, there is an opening being sealed by a sealing 70. Sealing 70, preferably, consists of a soft plastic material or of rubber. The use of the sample container 18 shown as a package for an injection pharmaceutical was already discussed above.

For the present invention it is important that the high frequency magnetic field $B_1$ excites magnetic resonance only within section A in which there is sample substance 62. The glass of which bulged portion 60 consists may remain out of consideration because glass does not generate resonance signals. Those elements, namely cap 68 and sealing 70, which, under certain circumstances, generate strong or at least measurable resonance signals, must be located outside the high frequency magnetic field $B_1$ or in the area of its stray field which does not excite measurable resonances.

Figure 5:
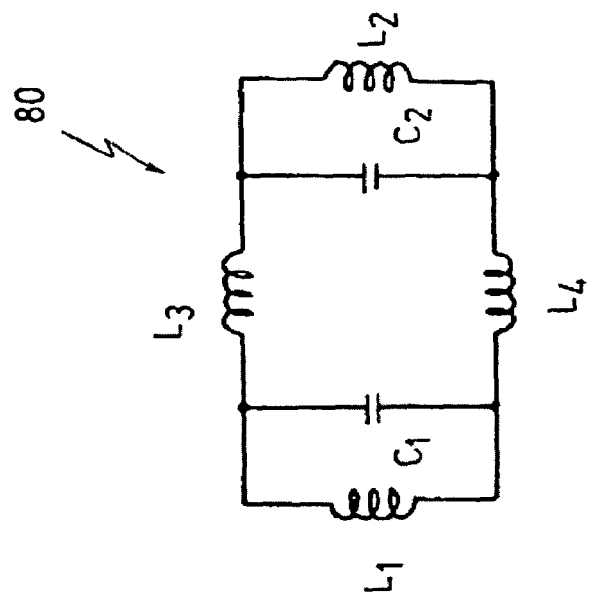
FIG. 5 is an electric equivalent circuit diagram of the probe head of FIGS. 2 to 4.

As can be seen from the depiction of FIG. 4 and the equivalent circuit diagram 80 of FIG. 5, the two annexes 44a and 44b constitute inductances $L_1$ and $L_2$. These inductances $L_1$ and $L_2$ are coupled to inductances $L_3$ and $L_4$ constituted by the two halves of ring 40 via capacities $C_1$ and $C_2$ configured by gaps 42a/46a and 42b/46b.

When probe head 24 is excited by a high frequency signal, a spatial distribution of the high frequency magnetic field $B_1$ is generated as shown in FIG. 3. Due to the already mentioned axial non-symmetry of probe head 24, the field lines of $B_1$ essentially extending parallel with respect to each other and transversely with respect to the field lines of constant magnetic field $B_0$ only within section A. As a consequence, magnetic resonance is solely excited in that section.

Probe head 24, therefore, allows to constitute an apparatus 10 permitting to weigh sample containers 18 with solid sample substance 62 in a conctacless manner, wherein a high rate of, for example, 180 sample containers per minute may be processed with a weighing accuracy of at least 1%.

Considering that apparatus 10 is preferably used within pharmaceutical installations, it is preferably configured such that it may be cleaned with liquid agents, in particular may be sterilized. When doing so, hot cleaning agents are used, having a temperature of about 70° C.

It goes, further, without saying, that apparatus 10 and probe head 24 may of course only be used to process liquid samples. In that case, means of the type already mentioned are required for generating a sufficient magnetic bias of the liquid sample substance before the measuring of the magnetic resonance is initiated.

Finally, it goes without saying that apparatus 10 and probe head 24 may be equipped with further features which are known in the art of magnetic resonance, for example with an internal standard for controlling the constant magnetic field. This is particularly appropriate when the magnet system is exposed to a cleaning operation at the above-mentioned high temperatures, because then the field strength needs a considerable re-calibration.

What is claimed is:

1. An apparatus configured for determining, by means of magnetic resonance, a quantitative property of each of a plurality of sample substances, wherein each sample substance is contained in a predetermined section of a separate sample container, the apparatus comprising:
   a conveyor configured for conveying said sample containers through a measuring station;
   a magnet system configured for generating a constant magnetic field of high homogeneity within the measuring station through which the sample containers are moved in a conveying direction;
   a split-ring resonator in the shape of a cylinder with a central axis arranged perpendicular to the conveying direction and having two diametrically-opposed gaps extending through the cylinder parallel to the central axis, each cylinder gap having adjacent thereto an annex extending parallel to the central axis, the annexes having heights greater than the cylinder height and broad surfaces in the measuring station between which each sample container passes;
   a transmitter receiver that feeds a high frequency signal to the split ring resonator so that a high frequency magnetic field is generated and received substantially only in the predetermined section of each sample container when that sample container is in the measuring station; and
   a magnetic resonance measuring unit at the measuring station configured for determining the quantitative property of each sample substance by means of magnetic resonance signals obtained from each sample substance contained within the predetermined section of each sample container when each is located at or within the measuring station.

2. The apparatus of claim 1 wherein each annex is C-shaped with an annex gap that communicates with an adjacent cylinder gap.

3. The apparatus of claim 2, characterized in that said annexes are wing-shaped.

4. The apparatus of claim 2, wherein the central axis is vertical.

5. The apparatus of claim 4, wherein the conveying direction is horizontal.

6. The apparatus of claim 1, wherein at least said measuring station is adapted to be cleaned by means of a liquid cleaning agent.

7. An NMR probe head fed by a transmitter receiver in order to generate and receive a high frequency magnetic field in each of a plurality of sample substances, wherein each sample substance is contained in a predetermined section of a separate sample container, the NMR probe head comprising:
   a split-ring resonator in the shape of a cylinder with a central axis and having two diametrically-opposed gaps extending through the cylinder parallel to the central axis; and
   an annex located adjacent to each cylinder gap and extending parallel to the central axis, the annexes having heights greater than the cylinder height and parallel broad surfaces defining a passageway perpendicular to the central axis through which each sample container passes, the cylinder and annexes arranged so that the generated and received high frequency magnetic field in each of a plurality of sample substances, is generated and received substantially only in the predetermined section of each sample container when that sample container is in the passageway.

8. The probe head of claim 7 wherein each annex is C-shaped with an annex gap that communicates with an adjacent cylinder gap.

9. The probe head of claim 8, characterized in that said annexes are wing-shaped.

10. The probe head of claim 8, wherein the central axis is vertical.

11. The apparatus of claim 10, wherein the passage way is horizontal.

* * * * *